United States Patent [19]

Kim et al.

[11] Patent Number: 5,677,456

[45] Date of Patent: Oct. 14, 1997

[54] QUINOLONE DERIVATIVES AND PROCESSES FOR THE PREPARATION THEREOF

[75] Inventors: Wan Joo Kim; Tae Ho Park; Moon Hwan Kim; Jewn Giew Park; Bong Jin Kim, all of Daejeon, Rep. of Korea

[73] Assignee: Korean Research Institute of Chemical Technology, Daejeon, Rep. of Korea

[21] Appl. No.: 438,886

[22] Filed: May 10, 1995

Related U.S. Application Data

[62] Division of Ser. No. 277,601, Jul. 20, 1994.

[30] Foreign Application Priority Data

Dec. 9, 1993 [KR] Rep. of Korea .................. 93-27871

[51] Int. Cl.$^6$ .................................................. C07D 471/04
[52] U.S. Cl. .................................................. 546/113
[58] Field of Search .............................. 546/113; 514/300

[56] References Cited

U.S. PATENT DOCUMENTS 4,946,844  8/1990  Tomari ........................... 514/254

FOREIGN PATENT DOCUMENTS

523512A1   7/1992   European Pat. Off. .
550903A1  12/1992   European Pat. Off. .

OTHER PUBLICATIONS

Mar., J. Advanced Organic Chemistry. Second Edition (1977). McGraw Hill—pp. 382, 384.

*Primary Examiner*—C. Warren Ivy
*Assistant Examiner*—Evelyn Huang
*Attorney, Agent, or Firm*—Brumbaugh, Graves, Donohue & Raymond

[57] ABSTRACT

The present invention relates to optical isomers of quinoline compounds of Formula (IA) or Formula (IA'), their pharmaceutically acceptable salts and their intermediates:

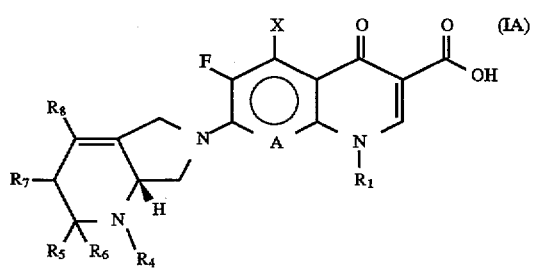

(IA)

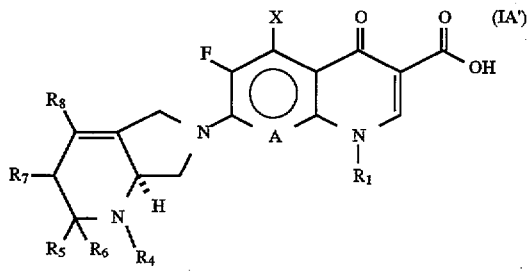

(IA')

In the above formulae, A represent nitrogen or

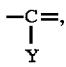

in which Y represents hydrogen, halogen such as fluorine or chlorine, lower alkyl or lower alkoxy such as methoxy, or together with $R_1$ forms —$CH_2CH_2CH_2$—, —$CH_2CH_2CH(CH_3)$—, —$OCH_2CH_2$—, —$OCH_2CH(CH_3)$—, —$SCH_2CH_2$— or —$SCH_2CH(CH_3)$—;

$R_1$ is as defined above or represents straight chain or cyclic lower alkyl group having 1 to 3 carbon atoms, a straight chain or cyclic lower alkyl group having 1 to 3 carbon atoms which is substituted with a halogen atom, a phenyl group or a phenyl group substituted with one or two halogen atoms, such as ethyl, cyclopropyl or 2,4-difluorophenyl;

$R^4$ represents hydrogen, lower alkyl, lower alkoxy, or an amino-protecting group, such as methyl, ethyl or butoxycarbonyl;

$R_5$, $R_6$, $R_7$ and $R_8$ may be the same or different and represent independently hydrogen, lower alkyl optionally substituted by amino, hydroxy or halogen, such as methyl or ethyl; and X represents hydrogen, halogen such as fluorine or chlorine, amino or lower alkyl such as methyl.

6 Claims, No Drawings

QUINOLONE DERIVATIVES AND PROCESSES FOR THE PREPARATION THEREOF

This application is a division of application Ser. No. 08/277,601, filed Jul. 20, 1994.

The present invention relates to novel quinolone compounds, pharmaceutically acceptable salts and optical isomers thereof which possess a broad antibacterial spectrum and exhibit strong antibacterial activity and to processes for preparing these quinolone compounds.

The present invention also relates to optical isomers of diazabicycloalken derivatives, which may be introduced to the above quinoline compounds, and to processes for preparing the diazabicycloalkene derivatives.

Representatives of the commercially available quinolone antibacterial agents include enoxacin, norflaxacin, oflaxacin, ciprofloxacin and tosufloxacin. However, it is generally known that these quinolone antibacterials exhibit relatively weak antibacterial activity against Gram-positive bacteria. Furthermore, quinolone-resistant strains have been frequently reported.

Thus, there is still a need for the development of quinolone antibacterials which not only show a broad antibacterial spectrum but also exert strong antibacterial activity against the quinolone-resistant strains.

An objects of the present invention is also to provide optical isomers of quinoline compounds of Formula (IA) or Formula (IA') and their pharmaceutically acceptable salts.

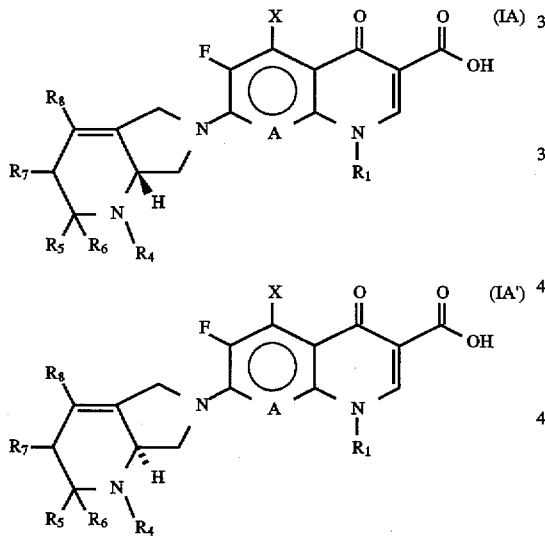

In the formulae, A represent nitrogen or

in which Y represents hydrogen, halogen such as fluorine or chlorine, lower alkyl or lower alkoxy such as methoxy, or together with R₁ forms —CH₂CH₂CH₂—, —CH₂CH₂CH(CH₃)—, —OCH₂CH₂—, —OCH₂CH(CH₃)—, —SCH₂CH₂— or —SCH₂CH(CH₃)—;

R₁ is as defined above or represents a straight chain alkyl group having 1 to 3 carbon atoms, which is optionally substituted with a halogen atom, or a cyclopropyl group which is optionally substituted with a halogen atom, a phenyl group or a phenyl group substituted with one or two halogen atoms, such as ethyl, cyclopropyl or 2,4-difluorophenyl;

$R_4$ represents hydrogen, lower alkyl, lower alkoxy, or an amino-protecting group, such as methyl, ethyl or butoxycarbonyl;

$R_5$, $R_6$, $R_7$ and $R_8$ may be the same or different and represent independently hydrogen, lower alkyl optionally substituted by amino, hydroxy or halogen, such as methyl or ethyl; and X represents hydrogen, halogen such as fluorine or chlorine, amino or lower alkyl such as methyl.

Lower alkyl is preferably $C_{1-6}$ alkyl, more preferably $C_{1-4}$, such as methyl or ethyl.

Another object of the present invention is to provide optical isomers represented by Formula (Ia) or (Ia');

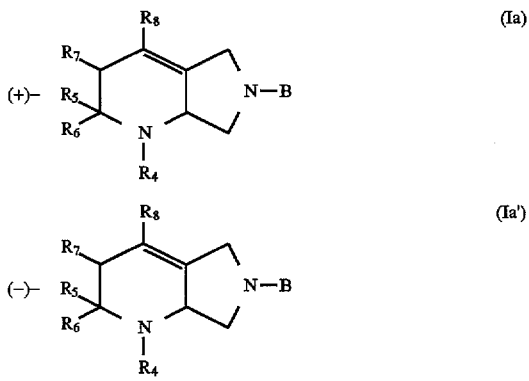

wherein $R_4$, $R_5$, $R_6$, $R_7$ and $R_8$ are the same as defined above, and B is hydrogen, lower alkyl, lower alkoxy, or an amino-protecting group, such as methyl, ethyl or butoxycarbonyl.

Preferred compounds of Formula (IA) or (IA') of the present invention which show strong antibacterial activity and posses a broad antibacterial spectrum are:

1-cyclopropyl-6-fluoro-7-(((+)-2,8-diazabicyclo[4.3.0]non-5-en)-8-yl)-8-methoxy-1,4-dihydro-4-oxo-3-quinoline carboxylic acid;

1-cyclopropyl-6-fluoro-7-(((−)-2,8-diazabicyclo[4.3.0]non-5-en)-8yl)-8-methoxy-1,4-dihydro-4-oxo-3-quinoline carboxylic acid;

1-cyclopropyl-6-fluoro-7-(((+)-2,8-diazabicyclo[4.3.0]non-5-en)-8-yl)-8-chloro-1,4-dihydro-4-oxo-3-quinoline carboxylic acid;

1-cyclopropyl-5-amino-6,8-difluoro-7-(((+)-2,8-diazabicyclo[4.3.0]non-5-en)-8-yl)-1,4-dihydro-4oxo-3-quinoline carboxylic acid;

9fluoro-3-(S)-methyl-10((+)-2,8-diazabicyclo[4.3.0]non-5en-8-yl)-7-oxo-2,3-dihydro-7H-pyrido[1,2,3-de]-[1,4]-benzoxazin-6-carboxylic acid; and pharmaceutically acceptable salts thereof.

Preferred Compounds of Formula (Ia) or (Ia') of the present invention are (+)-2,8-diazabicyclo[4.3.0]non-5-ene, and (−)-2,8-diazabicyclo[4.3.0]non-5-ene.

Compounds of Formula (Ia) and (IA') of the present invention may be prepared by the process illustrated below.

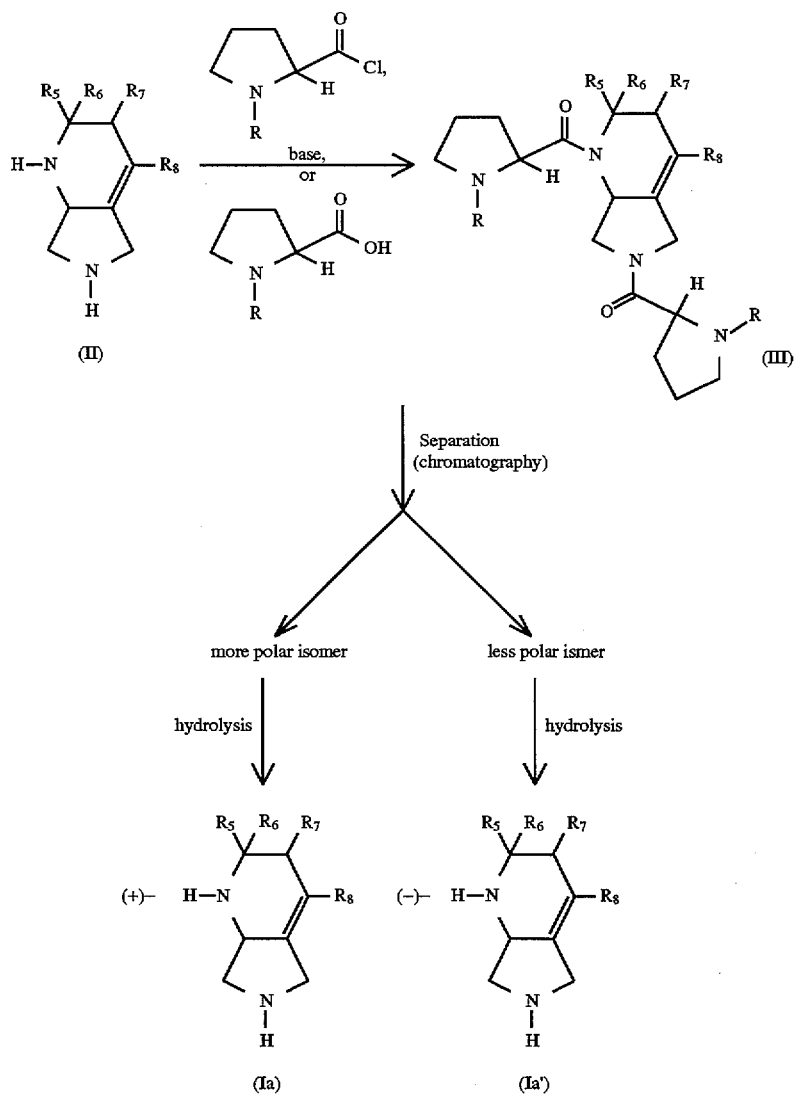

In the above formulae, $R_5$, $R_6$, $R_7$ and $R_8$ are the same as defined above, and R represents amine-protecting group such as toluenesulfonyl or t-butoxycarbonyl.

Compound (II) is reacted with N-tosyl-L-prolyl chloride in an organic solvent such as methylene chloride or chloroform or in a mixture of water and the said organic solvents in the presence of an organic base such as triethylamine, 1,8-diazabicylclo[5.4.0]undec-7-ene (DBU) and 1,5-diazabicyclo[4.3.0]non-5-ene (DBN) or an inorganic base such as sodium bicarbonate or sodium carbonate at −20° C. to 30° C. to give Compound (III). Compound (III) may also be prepared by reacting Compound (II) with N-protected L-proline in a solvent such as N,N-dimethylformamide (DMF), dimethyl sulfoxide (DMSO), acetonitrile or chloroform in the presence of an organic or inorganic base such as triethylamine, DBU or DBN and dicyclohexyl carbodiimide. Compound (III) is subjected to column chromatography and acid-catalized hydrolysis to obtain Compound (Ia) and Compound (Ia').

Compounds of Formula (IA) or Formula (IA") of the present invention may be prepared, using the compounds of Formula (Ia) or (Ia') above, by the process similar to processes described in U.S. patent application Ser. No. 08/052,711 filed Apr. 26, 1993.

The following examples are intended to further explain the present invention, without limiting the scope of the invention.

EXAMPLE 1

Preparation of (+)-2,8-diazabicyclo[4.3.0]non-5-ene dihydrogen chloride

Step (1): Preparation of N,N'-di-(N-tosyl-L-prolyl)-2,8-diazabicyclo[4.3.0]non-5-ene 4.8 g of 2,8-diazabicyclo[4.3.0]non-5-ene--therefore dihydrogen chloride and 13.5 ml of triethylamine were added to 100 ml of chloroform and the reaction mixture was stirred for 5 min. 14.0 g of N-tosyl-L-prolyl chloride in 100 ml of chloroform was added to the reaction mixture under cold temperature (below 0° C.) and the resulting reaction mixture was stirred for 3 hours at room temperature. The reaction mixture was diluted with 200 ml of chloroform, washed with 5% $NaHCO_3$ solution, next with 1N-HCl, and subsequently with NaCl solution, and dried with anhydrous magnesium sulfate. After evaporating the solvent under reduced pressure, the residue was subjected to silica gel column chromatography (ethyl acetate:methanol(v/v)=20:1) to obtain 6.6 g of more polar optical isomer of N,N'-di-(N-tosyl-L-prolyl)-2,8-diazabicyclo[4.3.0]non-5-ene and 5.79 g of less polar optical isomer of N,N'-di-(N-tosyl-L-prolyl)-2,8-diazabicyclo[4.3.0]non-5-ene.

more polar optical isomer: $[\alpha]^{20}_D=-3.4°(c=1.0, CH_3CH_2OH)$
$^1$H-NMR(CDCl$_3$, δ); 1.7~2.35(9H, m), 2.45(3H, s), 2.52 (3H, s) 3.25~3.60(6H, m), 3.52(1H, m), 3.29(1H, d), 4.13(1H, d), 4.33(1H, t), 4.40(1H, t), 4.60(2H, m), 5.95 (2H, br, s), 7.30(4H, dxd), 7.72(4H, dxd)

less polar optical isomer: $[\alpha]^{20}_D=-236.7°$ (c=1.0, CH$_3$CH$_2$OH)
$^1$H-NMR(CDCl$_3$, δ); 1.61(1H, m), 1.8~2.2(9H, m), 2.30~2.42(6H, dxd), 3.0~3.55(6H, m), 3.9~4.35(3H, m), 4.40~5.0(4H, m), 6.0(1H, m), 7.30(4H, m), 7.75(4H, m)

Step (2): Preparation of (+)-N,N'-di-t-butoxycarbonyl-2,8-diazabicyclo[4.3.0]non-5-ene To 20 ml of ethanol and 100 ml of 8N-HCl solution was added 7.02 g of the more polar optical isomer of N,N'-di-(N-tosyl-L-prolyl)-2,8-diazabicyclo[4.3.0]non-5-ene and the reaction mixture was stirred for 3 hours under reflux. The resulting reaction mixture was cooled to room temperature and the solvent was evaporated under reduced pressure. To the residue were added 100 ml of methanol and 12.5 ml of triethylamine and the resulting mixture was stirred for 10 min. 9.8 g of di-ti-butyldicarbonate was added to the reaction mixture and stirred for 10 hours at room temperature. The reaction solvent was evaporated under reduced pressure. The residue was dissolved in 100 ml of chloroform, washed with water, next with 5% acetic acid and subsequently with NaCl solution, and dried with anhydrous magnesium sulfate. The solvent was evaporated under reduced pressure and the residue was subjected to silica gel column chromatography (ethyl acetate:hexane (v/v)=6.1) to obtain 3.0 g of desired compound (yield: 83%).

$^1$H-NMR(CDCl$_3$, δ); 1.45(9H, s), 1.47(9H, s), 2.15(2H, m), 2.8~2.9(2H, m), 3.9(3H, t), 4.05(1H, t), 4.3~4.4(1H, m), 5.85(1H, br, s)
$[\alpha]^{20}$hd D=+179° (c=1.0, MeOH)

Step (3): Preparation of (30)-2,8-diazabicyclo[4.3.0] non-5-ene dihydrogen chloride 3.02 g of (+)-N,N'-di-t-butoxycarbonyl-2,8-diazabicyclo [4.3.0]non-5-ene was dissolved in 18 ml of 8% HCl-methanol solution and stirred for 12 hours at room temperature. The solvent was evaporated under reduced pressure and the 5 ml of ethanol was added to the residue and stirred to give white solid product. The white solid was filtered, washed with mixed solution of ethanol and ethyl ether and dried under reduced pressure to give 1.26 g of desired white solid product (yield: 69%).
$^1$H-NMR(CDCl$_3$, δ); 2.4(2H, m), 3.1~3.3(2H, m), 3.5~3.65 (1H, m), 3.8~4.1(3H, m), 4.2~4.4(1H, m), 6.05(1H, br, s)

$[\alpha]^{20}_D=1.4°$ (c=27.2, H$_2$O)

EXAMPLE 2

Preparation of (−)-2,8-diazabicyclo[4.3.0]-5-enedihydrogen chloride 7.2 g of the less polar optical isomer of N,N'-di-(N-tosyl-L-prolyl)-2,8-diazabicyclo[4.3.0]non-5-ene was treated by the process described in Steps (2) and (3) of Example 1 to give 1.14 g of desired compound.

$[\alpha]^{20}_D=-1.4°$ (c=27.2, H$_2$O)

EXAMPLE 3

Preparation of 1-cyclopropyl-6-fluoro-7-(((+)-2,8-diazabicyclo[4.3.0]non-5-en)-8-yl)-8-methoxy-1,4-dihydro-4-oxo-3-quinoline carboxylic acid 195 mg of (+)-2,8-diazabicyclo[4.3.0]non-5-ene dihydrogen chloride, 457 mg of DBU and 295 mg of 1-cyclopropyl-6,7-difluoro-8-methoxy-1,4-dihydro-4-oxo-3-quinoline carboxylic acid were added to 2.5 ml of acetonitrile and stirred for 10 hours under reflux. The reaction mixture was cooled to room temperature to result in solid products. The resulting solid product was filtered, washed with 3 ml of acetonitrile and dried to give 312 mg of desired white solid product.

$^1$H-NMR(CDCl$_3$, δ); 1.16(4H, m), 2.11(1H, m), 2.70~4.20 (7H, m), 4.02(3H, s), 4.65(1H, d), 5.70(1H, s), 7.84(1H, d), 8.80(1H, s)

EXAMPLE 4

Preparation of 1-cyclopropyl-6-fluoro-7-(((−)-2,8-diazabicyclo[4.3.0]non-5en)-8-yl)-8-methoxy-1,4-dihydro-4-dihydro-4-oxo-3-quinoline carboxylic acid 195 mg of (−)-2,8-diazabicyclo[4.3.0]non-5ene dihydrogen chloride was treated by the process described in Example 3 to give 296 mg of desired compound.

EXAMPLE 5

Preparation of 1-cyclopropyl-6-fluoro-7-(((+)-2,8-diazabicyclo[4.3.0]-non-5-en)-8-yl)-8-chloro-1,4-dihydro-4-oxo-3-quinoline carboxylic acid 195 mg of (+)-2,8-diazabicyclo[4.3.0]non-5-ene dihydrogen chloride and 299.5 mg of 1-cyclo-propyl-6,7-difluoro-8-chloro-1,4-dihydro-4-oxo-3-quinoline carboxylic acid were treated by the process described in Example 3 to give 346 mg of desired compound.

$^1$H-NMR(CDCl$_3$, δ); 1.20(4H, m), 2.10(1H, m), 2.30(1H, m), 2.65~4,10(7H, m), 4.93(1H, m), 5.10(1H, m), 5.63 (1H, m), 7.56(1H, d), 8.61(1H, s)

EXAMPLE 6

Preparation of 1-cyclopropyl-5-amino-6,8-difluoro-7-(((+)-2,8-diazabicyclo[4.3.0]non-5-en)-8-yl)-1,4-dihydro-4-oxo-3-quinoline carboxylic acid 195 mg of (+)-2,8-diazabicyclo[4.3.0]non-5ene dihydrogen chloride and 298 mg of 1-cyclo-propyl-5-amino-6,7,8-trifluoro-1,4-dihydro-4-oxo-3-quinoline carboxylic acid were treated by the process described in Example 3 to give 298 mg of desired compound.

$^1$H-NMR(CDCl$_3$, δ); 1.15(4H, m), 2.1(1H, m), 2.3(1H, m), 2.95(1H, m), 3.2~4.0(6H, m), 4.65(1H, d), 5.75(1H, s), 8.90(1H, s)

EXAMPLE 7

Preparation of 9-fluoro-3-(S)-methyl-10-(((+)-2,8-diazabicyclo[4.3.0]non-5en)-8-yl)-7-oxo-2,3-dihydro-7H-pyrido[1,2,3-de]-[1,4]-benzoxazin-6-carboxylic acid 200 mg of (+)-2,8-diazabicyclo[4.3.0]non-5ene dihydrogen chloride and 280 mg of 9,10-difluoro-3-(S)-methyl-7- oxo-2,3-dihydro-7H-pyrido[1,2,3-de]-[1,4]-benzoxaxin-6-carboxylic acid were treated by the process described in Example 3 to give 250 mg of desired compound.

$^1$H-NMR(CDCl$_3$, δ); 1.5(3H, d), 2.0(1H, m), 2.85(1H, m), 3.15(1H, m), 3.3~3.6(4H, m), 3.7(1H, m), 3.9(2H, m), 4.2~4.65(4H, m), 5.65(1H, br, s), 7.55(1H, d) 8.5(1H, s)

In Vitro Antibacterial Activity Test

The antibacterial activity of the compounds of the present invention was demonstrated in Table 1. The antibacterial activity was determined in accordance with the agar culture medium two-fold dilution method (Hoechst 345) by using a Muller-Hinton agar medium. Hoechst standard strains were used as the test strains. The strains having 10$^7$ CFU/ml were inoculated on the culture medium, and the growth of the strains was observed after incubating them at 37° C. for 18 hours, in which ciprofloxacin was used as a control material.

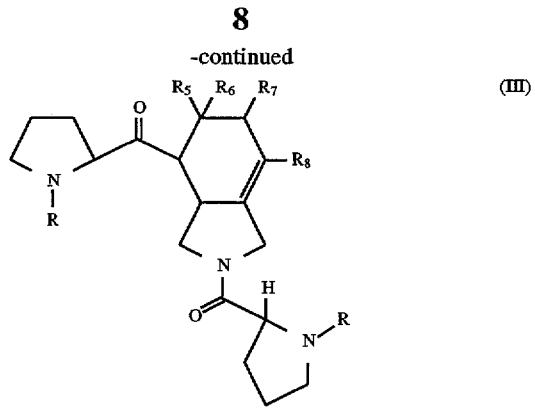

TABLE 1

| Strain/Substance | Example 3 | Example 4 | Example 5 | Example 6 | Example 7 | ciprofloxacin |
|---|---|---|---|---|---|---|
| *Streptococcus pyogenes* 308A | 0.195 | 0.781 | 0.195 | 0.098 | 0.781 | 3.125 |
| *Streptococcus pyogenes* 77A | 0.098 | 0.391 | 0.098 | 0.098 | 0.195 | 0.781 |
| *Streptococcus faecium* MD8b | 0.098 | 0.195 | 0.098 | 0.049 | 0.195 | 0.781 |
| *Staphylococcus aureus* SG511 | 0.025 | 0.098 | 0.025 | 0.007 | 0.098 | 0.195 |
| *Staphylococcus aureus* 285 | 0.025 | 0.098 | 0.025 | 0.013 | 0.195 | 0.391 |
| *Staphylococcus aureus* 503 | 0.013 | 0.049 | 0.025 | 0.004 | 0.098 | 0.781 |
| *Escherichia coli* O 78 | 0.004 | 0.025 | 0.007 | <0.002 | 0.025 | <0.002 |
| *Escherichia coil* DC 0 | 0.195 | 1.563 | 0.195 | 0.098 | 0.391 | 0.195 |
| *Escherichia coil* DC 2 | 0.025 | 0.098 | 0.025 | 0.025 | 0.098 | 0.098 |
| *Escherichia coil* TEM | 0.013 | 0.049 | 0.013 | <0.002 | 0.049 | 0.007 |
| *Escherichia coil* 1507E | 0.013 | 0.098 | 0.013 | 0.004 | 0.049 | 0.007 |
| *Pseudomonas aeruginosa* 9027 | 1.563 | 3.125 | 0.781 | 0.781 | 0.781 | 0.391 |
| *Pseudomonas aeruginosa* 1592B | 0.781 | 1.563 | 0.391 | 0.391 | 0.391 | 0.195 |
| *Pseudomonas aeruginosa* 1771 | 0.781 | 1.563 | 0.391 | 0.391 | 0.781 | 0.195 |
| *Pseudomonas aeruginosa* 1771M | 0.195 | 0.781 | 0.195 | 0.098 | 0.195 | 0.049 |
| *Salmonella typhimurium* | 0.007 | 0.049 | 0.007 | 0.004 | 0.025 | 0.007 |
| *Klebsiella aerogenes* 1082E | <0.002 | 0.007 | <0.002 | 0.007 | 0.013 | <0.002 |
| *Klebsiella aerogenes* 1552E | 0.025 | 0.098 | 0.013 | 0.007 | 0.098 | 0.013 |
| *Enterobacter cloacae* P 99 | 0.004 | 0.025 | 0.007 | <0.002 | 0.049 | 0.007 |
| *Enterobacter cloacae* 1321E | 0.004 | 0.025 | 0.004 | <0.002 | 0.025 | <0.002 |

What is claimed is:

1. A process for preparing a purified chemical compound of Formula (Ia) or (Ia') which comprises:

(a) reacting compound (II) with N-tosyl-L-prolyl chloride in an organic solvent or a mixture of said organic solvent and water in the presence of an organic or inorganic base to give the compound of Formula (III); and (b) conducting column chromatography followed by acid-catalyzed hydrolysis to obtain a purified chemical compound of formula (Ia) or (Ia'):

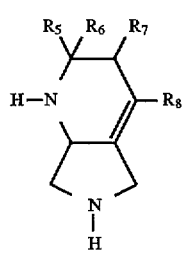

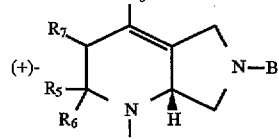

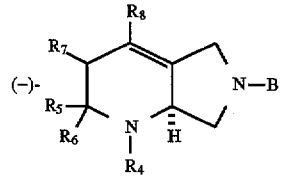

wherein R$_4$, represents a hydrogen atom;
R$_5$, R$_6$, R$_7$ and R$_8$ may be the same or different and each represents a radical selected from the group consisting of a hydrogen atom, a lower alkyl group a lower alkyl group substituted by an amino group, a hydroxy group, and a halogen atom,
B is a hydrogen atom; and
R is a tosyl group.

2. A process for preparing a purified chemical compound of Formula (Ia) or (Ia') which comprises:

(a) reacting compound (II) with N-protected L-proline in an organic solvent of a mixture of said organic solvent and water in the presence of an organic or inorganic base to give the compound of Formula (III); and (b) conducting column chromatography followed by acid-catalyzed hyrolysis to obtain a purified chemical compound of formula (Ia) or (Ia'):

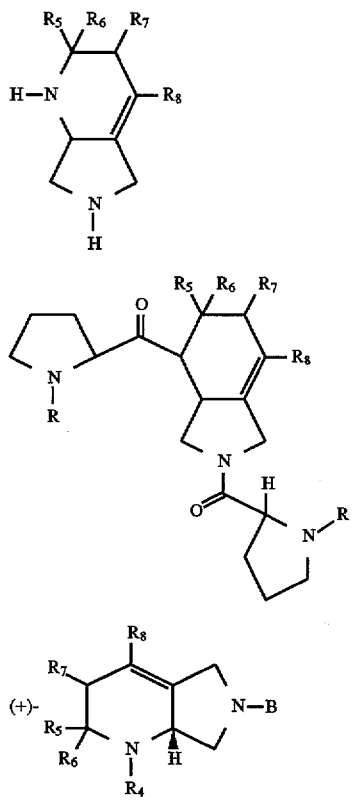

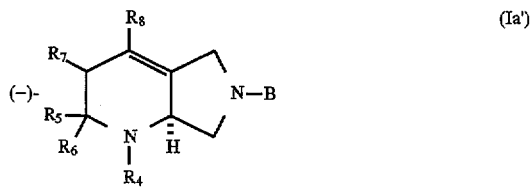

wherein, $R_4$, represents a hydrogen atom;

$R_5$, $R_6$, $R_7$ and $R_8$ may be the same or different and each represents a radical selected from the group consisting of a hydrogen atom, a lower alkyl group a lower alkyl group substituted by an amino group, a hydroxy group, and a halogen atom, B is a hydrogen atom; and R is an amino-protecting group.

3. A process according to claim 1 wherein the compound (II) is reacted with N-tosyl-L-proly chloride at a temperature of −20° to 30° C.

4. A process according to claim 2 wherein the compound (II) is reacted with N-protected L-proline at a temperature of −20° to 30° C.

5. A process according to claim 1 wherein the organic solvent is chloroform.

6. A process according to claim 2 wherein the organic solvent is chloroform.

* * * * *